US00PP24103P3

(12) United States Plant Patent
Egger

(10) Patent No.: US PP24,103 P3
(45) Date of Patent: Dec. 17, 2013

(54) ***HEUCHERA* PLANT NAMED 'SPELLBOUND'**

(50) Latin Name: ***Heuchera* spp.**
Varietal Denomination: Spellbound

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 149 days.

(21) Appl. No.: 13/385,795

(22) Filed: Mar. 6, 2012

(65) Prior Publication Data

US 2013/0239278 P1 Sep. 12, 2013

(51) Int. Cl.
*A01H 5/00* (2006.01)

(52) U.S. Cl.
USPC ..... Plt./440

(58) Field of Classification Search
USPC ..... Plt./440
See application file for complete search history.

(56) References Cited

PUBLICATIONS

Trademark Electronic Search System retrieved on Sep. 12, 2013. Retrieved from the Internet at <http://tess2.uspto.gov/bin/showfield?f=doc&state=4803:64uk09.2.2> 2 pp.*

* cited by examiner

*Primary Examiner* — June Hwu
(74) *Attorney, Agent, or Firm* — Klarquist Sparkman, LLP

(57) ABSTRACT

A new and distinct hybrid of *Heuchera* plant characterized by red purple spring leaves to silver with a dark purple margin summer leaves, medium-large, lightly ruffled, deeply lobed leaves, dark veins and leaf backs, multicolored flowers of yellow green, brown, and white on dark burgundy flowering stems, a large mounding habit, excellent vigor.

2 Drawing Sheets

Botanical denomination: *Heuchera* spp.
Variety designation: 'Spellbound'.

BACKGROUND OF THE INVENTION

The present invention relates to a new and distinct cultivar of *Heuchera* hybrid and given the cultivar name of 'Spellbound'. *Heuchera* is in the family Saxifragaceae. *Heuchera* 'Spellbound' originated from a planned breeding cross between *Heuchera* K132-2, a proprietary unreleased plant, as the seed parent, and *Heuchera* K170-1, a proprietary unreleased plant, as the pollen parent. Compared to the seed parent the new cultivar has darker foliage and a light rather than a heavy veil. Compared to the seed parent the new cultivar is smaller and has more purple.

Compared to *Heuchera* 'Plum Royale' (U.S. Plant Pat. No. 20,935) and *Heuchera* 'Sugar Plum' (U.S. Plant Pat. No. 21,857), the new cultivar is larger in habit and leaf size and has leaves that are deeply lobed and lightly ruffled and cupping upwards rather than cupping downwards and slightly lobed.

This new *Heuchera* is distinguished by:

1. red purple spring leaves to silver with a dark purple margin summer leaves,
2. medium-large, lightly ruffled, deeply lobed leaves,
3. dark veins and leaf backs,
4. multicolored flowers of yellow green, brown, and white on dark burgundy flowering stems,
5. a large mounding habit,
6. excellent vigor, This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a one-and-a-half-year-old plant of *Heuchera* 'Spellbound' grown outdoors in a 2 gallon container in May in Canby, Oreg.

FIG. 2 shows a close up of the flower of the same plant.

DETAILED PLANT DESCRIPTION

Figure 3:
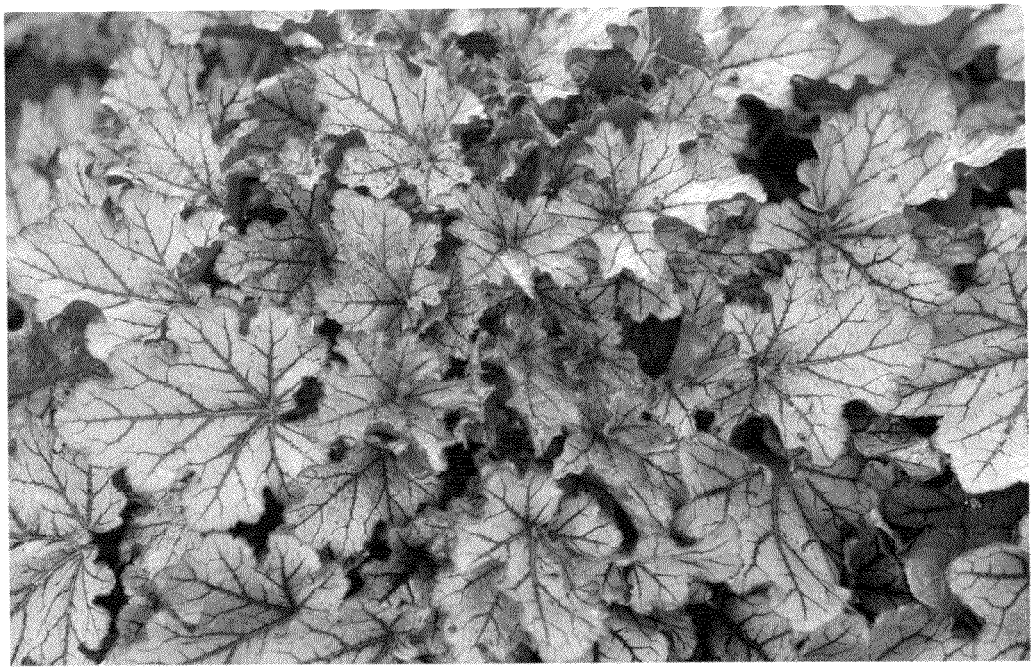
FIG. 3 shows the foliage of a 2 year plant growing in the ground in part sun in the trial field in October in Canby, Oreg.

The following is a detailed description of the new *Heuchera* cultivar based on observations taken in May of one-and-a-half-year-old specimens grown in a 2 gallon container outside in full sun in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5th edition.

Plant:

*Form*.—Basal rosette, herbaceous perennial.
*Hardiness*.—USDA Zone 4 to 9.
*Size*.—22 cm tall from top of the foliage to the ground and 50 cm wide.

*Habit*.—Mounding.
*Vigor*.—Excellent.
*Roots*.—Fibrous, freely branching, fine, and white in color; roots develop easily from cuttings.

Leaf:
*Type*.—Simple.
*Arrangement*.—Rosette.
*Number of leaves*.—30 to 50.
*Shape*.—Ovate to broadly ovate.
*Lobing/division*.—5 to 7 lobes, each with secondary lobes, the terminal is the longest.
*Venation*.—Palmate.
*Margins*.—Crenate and undulate.
*Apex*.—Mucronulate.
*Base*.—Cordate, lobes sometimes overlapping at the base.
*Blade size*.—Grows to 11.5 cm long and 11 cm wide.
*Surface texture*.—Glandular on both sides.
*Petiole description*.—12 cm to 19 cm long and 3 mm wide, glandular hairs, Purple N79B.
*Leaf color*.—Variable depending amount of light, temperature, and age of the leaf; spring topside Purple N77C with veins and margin Greyed Purple N186A, bottom side Purple N79A; summer through winter topside silver, closest to Greyed Purple N187B, tinged purple, N79A, with veins, Greyed Purple N187A, bottom side Greyed Purple N186C.

Inflorescence:
*Size*.—Grows to 23 cm long and 7 cm wide.
*Type*.—Thyrse.
*Number of flowers per thyrse*.—About 80 per thyrse.
*Number of thyrse*.—About 5 in first spring bloom.
*Peduncle*.—Grows to 33 cm tall, 3 mm wide at base, Purple N77A, glandular hairs, with no leaves.
*Pedicel*.—Variable in size, with glandular hairs, Purple N77A.
*Bloom period*.—May to August in Canby, Oreg.

Flower bud:
*Size*.—2.5 mm wide and 3 mm long.
*Description*.—Glandular puberulent, ovoid, down facing.
*Color*.—Yellow Green 146B heavily tinted Greyed Purple 187B.

Flower:
*Type*.—Perfect.
*Shape*.—Campanulate.
*Size*.—7 mm long and 5 mm wide.
*Petal description*.—5 in number, reflexed, 3 mm long and 0.5 mm wide, spatulate, tip obtuse, margin entire, glabrous on top side, glandular on bottom; White NN155B.
*Calyx description*.—Campanulate, 7 mm long and 5 mm wide, with 5 lobes, divided ½ way to the base, glandular hairs on both sides, obtuse, entire, Yellow Green 147C on inside and outside, with outside heavily tinted Greyed Purple 187B.
*Stamen description*.—5 in number, filaments 4 mm long, White NN155C, anthers 0.5 mm, Yellow Orange 21B, pollen none.
*Pistil description*.—1, 2-beaked, 6 mm long, Yellow Green 147C overall, ovary 2.5 mm, style 3.5 mm long.
*Fragrance*.—None.
*Lastingness*.—Each thyrse blooms for about 2 weeks on the plant.

Fruit:
*Type*.—Two beaked capsules.
*Size*.—3.5 mm deep by 5 mm wide.
*Fertility*.—Good.
*Color*.—Brown 200D.

Seed:
*Shape*.—Linear.
*Size*.—2 mm long.
*Color*.—Black, 202A.

Pest and disease tolerance: Excellent disease resistance to powdery mildew, the common problem of *Heuchera*. Susceptible to *Heuchera* rust and root weevils.

I claim:

1. A new and distinct hybrid of *Heuchera* plant as herein illustrated and described.

* * * * *

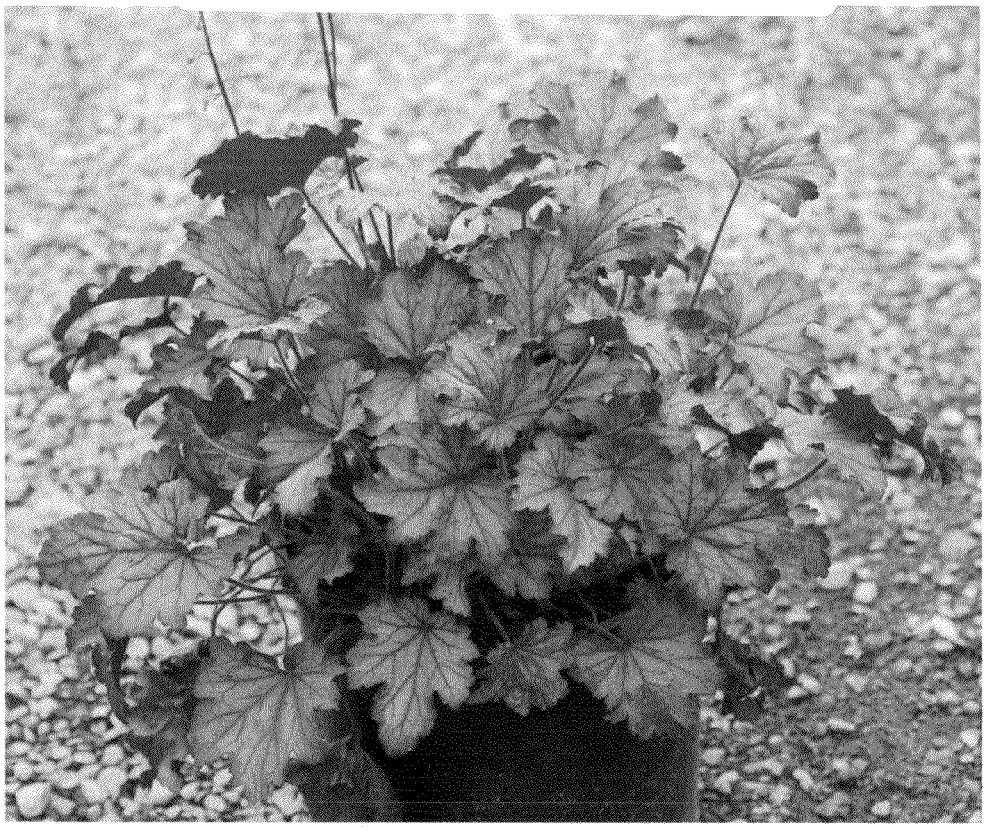
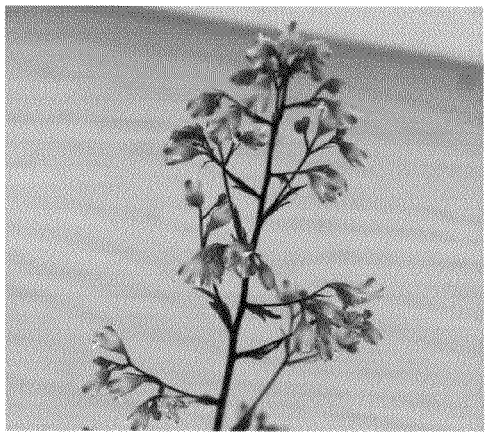
Fig. 1 above
Fig. 2 to left